United States Patent [19]

Komatsu et al.

[11] Patent Number: 5,607,861
[45] Date of Patent: Mar. 4, 1997

[54] METHOD FOR SPOTTING LIQUID SAMPLES ONTO FRAMELESS DRY-TYPE CHEMICAL ANALYSIS FILM PIECES

[75] Inventors: Akihiro Komatsu; Nobuaki Tokiwa, both of Kanagawa-ken; Yoshio Saito, Saitama-ken, all of Japan

[73] Assignee: Fuji Photo Film Co., Ltd., Kanagawa, Japan

[21] Appl. No.: 664,799

[22] Filed: Jun. 17, 1996

Related U.S. Application Data

[63] Continuation of Ser. No. 395,692, Feb. 28, 1995, abandoned.

[30] Foreign Application Priority Data

Apr. 15, 1994 [JP] Japan .................................. 6-077149

[51] Int. Cl.$^6$ ........................................ G01N 35/10
[52] U.S. Cl. .................... 436/50; 436/43; 436/46; 436/55; 422/63; 422/67; 422/105; 73/864.11; 141/351
[58] Field of Search ............... 436/43, 46, 50, 436/54, 174, 180, 807, 164, 165, 169, 170; 422/56, 57, 63, 64, 66, 67, 81, 100, 105, 107, 108, 110; 73/864.24, 864.25, 864.11; 141/130, 351, 352, 251, 258, 260, 263

[56] References Cited

U.S. PATENT DOCUMENTS

| | | | |
|---|---|---|---|
| 3,992,158 | 11/1976 | Przybylowicz et al. | 422/57 |
| 4,292,272 | 9/1981 | Kitajima et al. | 422/57 |
| 4,340,390 | 7/1982 | Collins et al. | 23/230 |
| 4,452,899 | 6/1984 | Alston | 436/46 |
| 4,675,301 | 6/1987 | Charneski et al. | 436/180 |
| 4,715,413 | 12/1987 | Backlund et al. | 141/94 |
| 4,794,085 | 12/1988 | Jessop et al. | 436/54 |
| 4,971,763 | 11/1990 | Columbus | 422/100 |
| 5,133,392 | 7/1992 | Hamann | 141/1 |
| 5,143,849 | 9/1992 | Barry et al. | 436/50 |
| 5,204,268 | 4/1993 | Matsumoto | 436/44 |
| 5,213,764 | 5/1993 | Kerr et al. | 422/100 |

Primary Examiner—Long V. Le
Attorney, Agent, or Firm—Sughrue, Mion, Zinn, Macpeak & Seas

[57] ABSTRACT

A predetermined amount of a liquid sample is accommodated in a sample spotting tip, which is fitted to a bottom end of a suction nozzle for sucking the liquid sample. Thereafter, the sample spotting tip is moved down, and the bottom end of the sample spotting tip is thereby brought into contact with a dry-type frameless chemical analysis film piece. The sample spotting tip is then moved up. The pressure inside the sample spotting tip is increased, while the sample spotting tip is thus being moved up. The liquid sample is thereby discharged from the sample spotting tip onto the dry-type frameless chemical analysis film piece.

2 Claims, 9 Drawing Sheets

METHOD FOR SPOTTING LIQUID SAMPLES ONTO FRAMELESS DRY-TYPE CHEMICAL ANALYSIS FILM PIECES

This is a Continuation of application Ser. No. 08/395,692 filed Feb. 28, 1995, now abandoned.

BACKGROUND OF THE INVENTION

1. Field of the Invention

This invention relates to a method and apparatus for spotting liquid samples onto dry-type frameless chemical analysis film pieces, wherein a liquid sample, such as blood or urine, is spotted onto a dry-type frameless chemical analysis film piece having a layer containing a reagent, which will undergo a chemical reaction, an immune reaction, or the like, with a specific biochemical substance contained in the liquid sample and will thereby give rise to a change in optical density. This invention particularly relates to a method and apparatus for spotting liquid samples onto dry-type frameless chemical analysis film pieces, wherein a liquid sample accommodated in a nozzle tip is discharged onto a dry-type frameless chemical analysis film piece.

2. Description of the Prior Art

Qualitative or quantitative analyses of specific chemical constituents in liquid samples are conducted for various industrial purposes. Particularly, it is very important in biochemical and clinical fields to be able to quantitatively analyze certain chemical or physical constituents in body fluids, such as blood or urine.

Recently, dry-type chemical analysis films were developed for use in systems designed for performing quantitative analyses, with which systems the amounts of specific chemical constituents or specific physical constituents contained in droplets of liquid samples spotted onto the dry-type chemical analysis films, are determined. Such dry-type chemical analysis films are disclosed in, for example, U.S. Pat. Nos. 3,992,158 and 4,292,272. It is possible to analyze liquid samples more simply and more quickly with methods in which the dry-type chemical analysis films are used than with methods in which a conventional wet-type analysis is carried out. Therefore, it is more desirable to use the dry-type chemical analysis films, particularly in medical organizations, research laboratories, or the like, where many samples must be analyzed, than to carry out the conventional wet-type analysis.

In order to use a dry-type chemical analysis film in the quantitative analysis of a chemical constituent, or the like, contained in a liquid sample, a droplet of the liquid sample is put on the dry-type chemical analysis film and is kept at a predetermined temperature (i.e. incubated) for a predetermined time in an incubator, which causes a color reaction. The dry-type chemical analysis film is then exposed to light having a wavelength, which is selected in advance. The selection of the wavelength depends on the specific biochemical substances contained in the liquid sample and the constituents of a reagent contained in the dry-type chemical analysis film. Light is thus irradiated to the dry-type chemical analysis film, and the optical density is found. The optical density depends on how much of a reaction product was formed by the reaction between the liquid sample and the reagent in the dry-type chemical analysis film. Thereafter, a calibration curve, which is created in advance and which represents the relationship between the optical densities and the concentrations of the specific biochemical substance in liquid samples, is used in order to determine the concentration of the biochemical substance in the liquid sample from the optical density, which has been found. Thereafter, the dry-type chemical analysis film, which has thus been used, is taken out of the incubator and put into a waste film box. A biochemical analysis system is constituted in this manner.

However, in general, the dry-type chemical analysis film described above is composed of a frame, which is constituted of a plastic material, and a dry-type chemical analysis film piece, which is sandwiched by the frame. The dry-type chemical analysis film piece comprises a substrate, which is constituted of a plastic material, or the like, a reagent layer containing a reagent, and a spreading layer, which layers are overlaid on the substrate. Therefore, the sizes of the accommodating section of the incubator, which accommodates the dry-type chemical analysis film and keeps its temperature at a predetermined value, a conveyance system for conveying the dry-type chemical analysis film, a supplier, which stores the dry-type chemical analysis film in the dry state before the liquid sample is supplied thereto, and a cartridge for housing the dry-type chemical analysis film, become large due to the provision of the frame on the dry-type chemical analysis film piece. Accordingly, the sizes of the incubator, the conveyance system, the supplier, and the cartridge cannot be kept small. Also, the capacity for accommodating the dry-type chemical analysis film, the capacity for conveying the dry-type chemical analysis film, and the capacity for storing the dry-type chemical analysis film become small. Therefore, the processing capacity of the biochemical analysis system cannot be kept large as a whole. Further, the cost for fitting the dry-type chemical analysis film piece to the frame cannot be kept low, and therefore the cost for the biochemical analysis cannot be kept low.

In view of the above circumstances, the applicant conducted extensive research in order to develop a technique for carrying out the biochemical analyses by using dry-type chemical analysis film pieces having no frame. For example, in European Patent Publication No. 634657A, the applicant proposed a biochemical analysis system comprising (i) a cartridge for accommodating a plurality of dry-type chemical analysis film pieces having no frame, (ii) a suction and take-out means, which may be constituted of a suction cup, or the like, and which takes each of the dry-type chemical analysis film pieces out of the cartridge such that they may not be scratched, (iii) a sample spotting means for spotting a predetermined amount of a liquid sample onto the dry-type chemical analysis film piece, which has been taken out of the cartridge by the suction and take-out means, and (iv) an incubator for keeping the dry-type chemical analysis film piece, to which the liquid sample has been spotted, at a predetermined temperature.

As the technique for spotting the liquid sample onto the dry-type chemical analysis film piece, it may be considered to directly use the technique for spotting the liquid sample onto the conventional dry-type chemical analysis film having a frame.

Specifically, for example, it may be considered to utilize the sample spotting technique, wherein a droplet of the liquid sample is formed at the bottom end of a sample spotting tip, the sample spotting tip is then moved down, and the bottom end of the sample spotting tip is thus moved to a position close to the surface of the dry-type chemical analysis film. The downward movement of the sample spotting tip is ceased when the droplet of the liquid sample comes into contact with the surface of the dry-type chemical analysis film, and the droplet is thereby spread on the surface of the dry-type chemical analysis film.

Also, it may be considered to utilize the sample spotting technique disclosed in, for example, U.S. Pat. No. 4,340,390. Specifically, the bottom end of a sample spotting tip is moved to a position at a predetermined distance d from the surface of a dry-type chemical analysis film, and thereafter a liquid sample contained in the sample spotting tip is discharged at a predetermined speed.

With the dry-type chemical analysis film provided with a frame, the flatness of the surface of the film can be kept unchanged. Therefore, even if a different dry-type chemical analysis film provided with a frame is used, the position of the surface of the film can be kept constant. However, in cases where dry-type chemical analysis film pieces having no frame are used, the degree of bending of the surface of the film surface varies for different film piece. Therefore, the position of the film surface cannot always be kept constant.

Specifically, if the conventional sample spotting techniques are applied to the dry-type chemical analysis film pieces having no frame, the distance between the bottom end of the sample spotting tip and the film surface will vary for different film piece.

If the distance between the bottom end of the sample spotting tip and the film surface becomes very large, the droplet of the liquid sample or the discharged flow of the liquid sample will break at the base portion of the droplet or the discharged flow, and part of the liquid sample will remain in the sample spotting tip without being spotted onto the dry-type chemical analysis film piece. Such problems will occur more readily in cases where the spreading speed of the liquid sample on the dry-type chemical analysis film piece is high and/or the viscosity of the liquid sample is low.

If the distance between the bottom end of the sample spotting tip and the film surface becomes very small, the level of the liquid sample being spread on the film surface will rise, and the bottom end of the sample spotting tip will become immersed in the discharged liquid sample. As a result, after the spreading of the liquid sample is finished, part of the liquid sample will cling to and remain on the outer side wall of the bottom end of the sample spotting tip. Such problems will occur more readily in cases where the spreading speed of the liquid sample on the dry-type chemical analysis film piece is low and/or the viscosity of the liquid sample is high.

A different sample spotting technique has been disclosed in, for example, U.S. Pat. No. 5,143,849. With the disclosed technique, a meniscus-like droplet of a liquid sample is formed at the bottom end of a sample spotting tip, and the sample spotting tip is then moved down. When the droplet comes into contact with the film surface, the contact is detected from a small change in the pressure inside the sample spotting tip, and the downward movement of the sample spotting tip is ceased. In this state, or after the sample spotting tip has been moved up a predetermined distance, the liquid sample is discharged from the sample spotting tip onto the film surface.

With the conventional sample spotting technique disclosed in U.S. Pat. No. 5,143,849, the distance between the bottom end of the sample spotting tip and the film surface can be controlled accurately, and therefore the problems encountered with the two conventional techniques described above do not occur. However, the size of the meniscus-like droplet of the liquid sample is small, and a comparatively long time is required to detect whether the droplet has been or has not been brought into contact with the film surface. Therefore, the speed, with which the sample spotting tip is moved down, cannot be kept high, and the sample spotting process cannot be carried out quickly.

A different sample spotting technique has also been disclosed in, for example, U.S. Pat. No. 5,133,392. With the disclosed technique, a sample spotting tip is pushed against a bottom surface of a container such that the sample spotting tip may be sealed. A pressure is applied inside the sample spotting tip, and the sample spotting tip is moved up. The separation of the sample spotting tip from the bottom surface of the container is detected by detecting that the pressure inside the sample spotting tip has become smaller than a threshold value. Thereafter, a pressure is further applied inside the sample spotting tip, the sample spotting tip is moved up, and a liquid sample is thereby discharged onto the bottom surface of the container.

With the conventional sample spotting technique disclosed in U.S. Pat. No. 5,133,392, the distance between the bottom end of the sample spotting tip and the bottom surface of the container can be controlled accurately. Therefore, the problems encountered with the two conventional techniques described above do not occur. However, the speed, with which the sample spotting tip is moved up, must be kept low such that the separation of the sample spotting tip from the bottom surface of the container can be detected. Therefore, the sample spotting process cannot be carried out quickly.

SUMMARY OF THE INVENTION

The primary object of the present invention is to provide a method for spotting liquid samples onto dry-type frameless chemical analysis film pieces, wherein a predetermined amount of a liquid sample is capable of being spread reliably on each of dry-type analytical film pieces having no frame, which have different degrees of bending of the film piece surface.

Another object of the present invention is to provide a method for spotting liquid samples onto dry-type frameless chemical analysis film pieces, wherein the speed, with which a sample spotting tip is moved down to each of dry-type analytical film pieces having no frame and having different degrees of bending of the film piece surface, is kept high, and the process for spotting liquid samples onto the dry-type analytical film pieces having no frame and having different degrees of bending of the film piece surface is carried out quickly.

The specific object of the present invention is to provide an apparatus for carrying out the method for spotting liquid samples onto dry-type frameless chemical analysis film pieces.

The present invention provides a method for spotting liquid samples onto dry-type frameless chemical analysis film pieces, comprising the steps of:

i) accommodating a predetermined amount of a liquid sample in a sample spotting tip, which is fitted to a bottom end of a suction nozzle for sucking the liquid sample, ii) moving the sample spotting tip down, the bottom end of the sample spotting tip being thereby brought into contact with a dry-type frameless chemical analysis film piece, iii) moving the sample spotting tip up, and iv) increasing the pressure inside the sample spotting tip, while the sample spotting tip is thus being moved up, whereby the liquid sample is discharged from the sample spotting tip onto the dry-type frameless chemical analysis film piece.

The method for spotting liquid samples onto dry-type frameless chemical analysis film pieces in accordance with the present invention may be modified such that, when the liquid sample is discharged from the sample spotting tip onto the dry-type frameless chemical analysis film piece, the speed, with which the sample spotting tip is moved up, and the pressure inside the sample spotting tip may be adjusted.

Also, the method for spotting liquid samples onto dry-type frameless chemical analysis film pieces in accordance with the present invention may be modified such that, after the predetermined amount of the liquid sample has been accommodated in the sample spotting tip, but before the bottom end of the sample spotting tip is brought into contact with the dry-type frameless chemical analysis film piece, the pressure inside the sample spotting tip may be reduced to a negative pressure, and air may thereby be sucked into the bottom end portion in the sample spotting tip.

The present invention also provides an apparatus for spotting liquid samples onto dry-type frameless chemical analysis film pieces, comprising:

i) a liquid sample sucking and discharging means, which sucks a predetermined amount of a liquid sample into a sample spotting tip fitted to a bottom end of a suction nozzle for sucking the liquid sample, and which thereafter discharges the liquid sample onto a dry-type frameless chemical analysis film piece, and ii) a nozzle vertical movement means, which moves the suction nozzle up and down, wherein, after the suction nozzle has been moved down to a predetermined position, at which the sample spotting tip accommodating the liquid sample therein comes into contact with the dry-type frameless chemical analysis film piece, a first vertical movement changeover means changes over the vertical movement of the suction nozzle from the downward movement to the upward movement, and wherein, when the vertical movement of the suction nozzle has been changed over from the downward movement to the upward movement, the suction nozzle is moved up by the nozzle vertical movement means, and the liquid sample is discharged by the liquid sample sucking and discharging means from the sample spotting tip onto the dry-type frameless chemical analysis film piece while the suction nozzle is being moved up by the nozzle vertical movement means.

The present invention further provides an apparatus for spotting liquid samples onto dry-type frameless chemical analysis film pieces, comprising:

i) a liquid sample sucking and discharging means, which sucks a predetermined amount of a liquid sample into a sample spotting tip fitted to a bottom end of a suction nozzle for sucking the liquid sample, and which thereafter discharges the liquid sample onto a dry-type frameless chemical analysis film piece, and ii) a nozzle vertical movement means, which moves the suction nozzle up and down, wherein a contact state detecting means is provided which detects that the bottom end of the sample spotting tip has been brought into contact with the dry-type frameless chemical analysis film piece when the sample spotting tip accommodating the liquid sample therein is moved down, wherein a second vertical movement change-over means is provided which changes over the vertical movement of the suction nozzle from the downward movement to the upward movement in accordance with a detection signal, the detection signal being generated by the contact state detecting means when the bottom end of the sample spotting tip has been brought into contact with the dry-type frameless chemical analysis film piece, and wherein, when the vertical movement of the suction nozzle has been changed over from the downward movement to the upward movement, the suction nozzle is moved up by the nozzle vertical movement means, and the liquid sample is discharged by the liquid sample sucking and discharging means from the sample spotting tip onto the dry-type frameless chemical analysis film piece while the suction nozzle is being moved up by the nozzle vertical movement means.

The apparatus for spotting liquid samples onto dry-type frameless chemical analysis film pieces in accordance with the present invention may be modified such that a control means may be provided for adjusting the speed, with which the sample spotting tip is moved up, and the pressure inside the sample spotting tip when the liquid sample is discharged from the sample spotting tip onto the dry-type frameless chemical analysis film piece.

With the method and apparatus for spotting liquid samples onto dry-type frameless chemical analysis film pieces in accordance with the present invention, before the liquid sample is discharged from the sample spotting tip onto the dry-type frameless chemical analysis film piece, the bottom end of the sample spotting tip is brought into contact with the surface of the dry-type frameless chemical analysis film piece. Therefore, even if the degree of bending of the film piece surface varies for different dry-type frameless chemical analysis film piece, and even if the height of the sample spotting tip fitted to the sample spotting nozzle and/or the height of the sample spotting nozzle fluctuates, the distance between the surface of the dry-type frameless chemical analysis film piece and the bottom end of the sample spotting tip can be recognized when the bottom end of the sample spotting tip is moved up after having been brought into contact with the surface of the dry-type frameless chemical analysis film piece. Therefore, the method and apparatus for spotting liquid samples onto dry-type frameless chemical analysis film pieces in accordance with the present invention are free of the problems in that, as with the conventional sample spotting techniques described above, the distance between the film surface and the bottom end of the sample spotting tip becomes very large or very small, and therefore part of the liquid sample remains in the region inside of the sample spotting tip or on the outer side wall of the bottom end of the sample spotting tip without being spotted onto the film surface. Accordingly, with the method and apparatus for spotting liquid samples onto dry-type frameless chemical analysis film pieces in accordance with the present invention, the predetermined amount of the liquid sample can be reliably spread on the dry-type frameless chemical analysis film piece. As a result, the accuracy, with which the liquid sample is analyzed, can be prevented from fluctuating.

In particular, the apparatus for spotting liquid samples onto dry-type frameless chemical analysis film pieces in accordance with the present invention should preferably be provided with the contact state detecting means, which detects that the bottom end of the sample spotting tip has been brought into contact with the dry-type frameless chemical analysis film piece. In such cases, when the bottom end of the sample spotting tip is moved up, the distance between the bottom end of the sample spotting tip and the dry-type frameless chemical analysis film piece can be recognized accurately.

Also, since the bottom end of the sample spotting tip is brought into contact with the dry-type frameless chemical analysis film piece, the position of the surface of the film piece can be recognized. Therefore, when the sample spotting tip is moved down, even if the bottom end of the sample spotting tip goes beyond the position of the surface of the dry-type frameless chemical analysis film piece, the dry-type frameless chemical analysis film piece will be bent, and the contact state of the bottom end of the sample spotting tip and the film piece surface can be kept. Further, it is not necessary to carry out the accurate operation for bringing the meniscus-like droplet into contact with the film surface as in the conventional sample spotting techniques described above. Accordingly, with the method and apparatus for spotting liquid samples onto dry-type frameless chemical analysis film pieces in accordance with the present invention, the speed, with which the sample spotting tip is moved down, can be kept high, and the process for spotting liquid samples onto the dry-type frameless chemical analysis film pieces can be carried out quickly.

Furthermore, since the bottom end itself of the sample spotting tip is brought into contact with the dry-type frameless chemical analysis film piece, the position of the surface of the film piece can be recognized. Therefore, the detection of the position of the surface of the film piece can be carried out more quickly than with the conventional sample spotting technique, in which the position of the film surface is detected by bringing the meniscus-like droplet formed at the bottom end of a sample spotting tip into contact with a film surface and detecting a small change in the pressure inside the sample spotting tip. In cases where the bottom end of the sample spotting tip goes beyond the position of the surface of the dry-type frameless chemical analysis film piece, the sample spotting tip may thereafter be moved up, and the position, at which the bottom end of the sample spotting tip separates from the surface of the dry-type frameless chemical analysis film piece, may be detected. The position thus detected may then be taken as the position of the surface of the dry-type frameless chemical analysis film piece.

The method and apparatus for spotting liquid samples onto dry-type frameless chemical analysis film pieces in accordance with the present invention should preferably be constituted such that the speed, with which the sample spotting tip is moved up, and the pressure inside the sample spotting tip can be adjusted. In such cases, the sample spotting process can be carried out appropriately in accordance with the kind of the dry-type frameless chemical analysis film piece used, the kind of the liquid sample, and the spreading rate of the liquid sample.

Moreover, the method and apparatus for spotting liquid samples onto dry-type frameless chemical analysis film pieces in accordance with the present invention should preferably be constituted such that, after the predetermined amount of the liquid sample has been accommodated in the sample spotting tip, but before the bottom end of the sample spotting tip is brought into contact with the dry-type frameless chemical analysis film piece, the pressure inside the sample spotting tip may be reduced to a negative pressure, and air may thereby be sucked into the bottom end portion in the sample spotting tip. In such cases, when the bottom end of the sample spotting tip is brought into contact with the dry-type frameless chemical analysis film piece, the liquid sample can be prevented from being spread on the film piece surface. Therefore, it is possible to prevent the problems from occurring in that a substance of the wetted film piece surface clings to the bottom end of the sample spotting tip and serves as an impurity during the next sample spotting process. Further, since the liquid sample is discharged from the sample spotting tip while the bottom end of the sample spotting tip is being moved away from the surface of the dry-type frameless chemical analysis film piece, even if there is a substance transferring from the film piece to the bottom end of the sample spotting tip when the bottom end of the sample spotting tip is brought into contact with the film piece, large effects of washing off the substance can be obtained.

BRIEF DESCRIPTION OF THE DRAWINGS

FIG. 8 is a flow chart showing a sequence program in a computer shown in FIG. 1, FIGS. 9A, 9B, 9C, 9D, and 9E are schematic views showing a different embodiment of the method for spotting liquid samples onto dry-type frameless chemical analysis film pieces in accordance with the present invention.

DESCRIPTION OF THE PREFERRED EMBODIMENTS

The present invention will hereinbelow be described in further detail with reference to the accompanying drawings.

Figure 2:
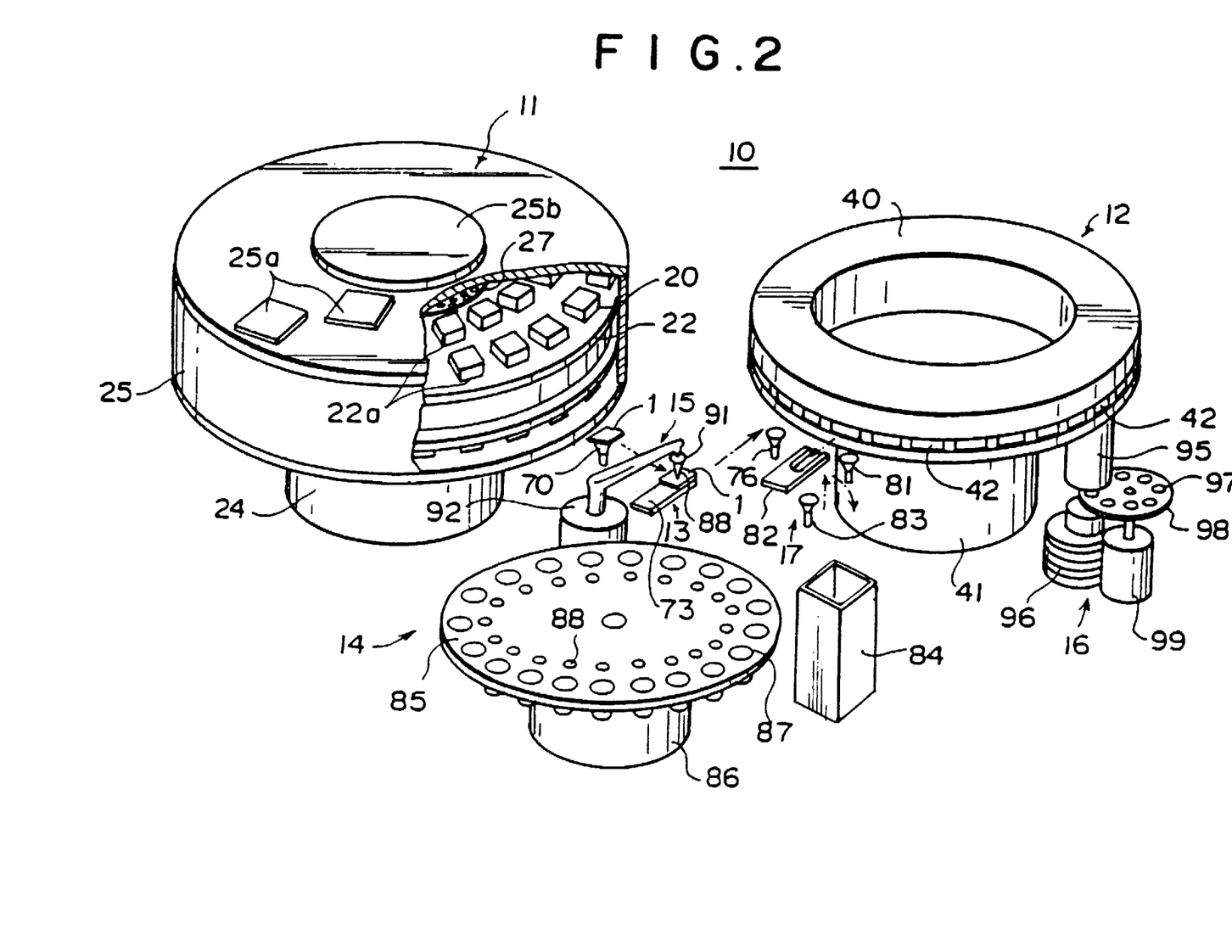
FIG. 2 is a perspective view showing a biochemical analysis system, in which the embodiment of FIG. 1 is utilized.

FIG. 2 is a perspective view showing a biochemical analysis system for carrying out an embodiment of the method for spotting liquid samples onto dry-type frameless chemical analysis film pieces in accordance with the present invention.

With reference to FIG. 2, a biochemical analysis system 10 comprises a film accommodating means (a film supplier) 11, which stores a plurality of unused rectangular dry-type frameless chemical analysis film pieces 1, 1, . . . , and an incubator 12, which is located beside the film accommodating means 11 and which keeps a dry-type frameless chemical analysis film piece 1 at a predetermined temperature for a predetermined time. The biochemical analysis system 10 also comprises a film conveyance means 13, which conveys a dry-type frameless chemical analysis film piece 1 from the film accommodating means 11 to the incubator 12, and a liquid sample accommodating means (a sampler) 14, which accommodates therein a plurality of kinds of liquid samples, such as serum and urine. The biochemical analysis system 10 further comprises a sample spotting means 15, which spots a liquid sample, which is accommodated in the liquid sample accommodating means 14, onto a dry-type frameless chemical analysis film piece 1, which is located on the conveyance path of the film conveyance means 13, and a measurement means 16, which is located under the incubator 12.

Figure 3:
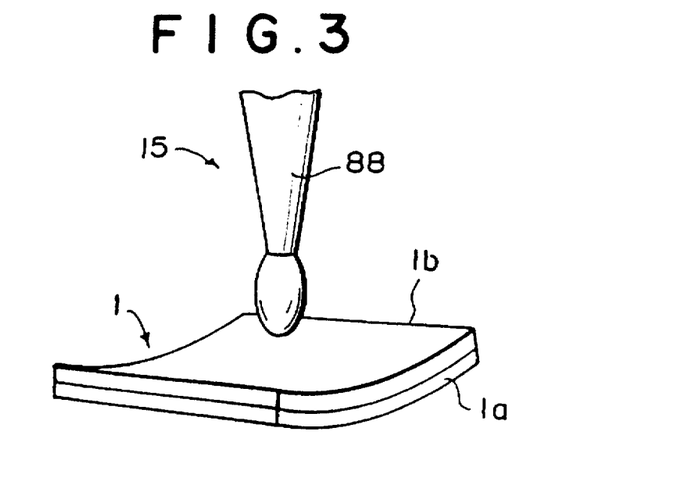
FIG. 3 is a perspective view showing how a liquid sample is spotted onto a dry-type frameless chemical analysis film piece.

As illustrated in FIG. 3, the dry-type frameless chemical analysis film piece 1 comprises a light transmitting substrate (a base film) 1a, which is constituted of a plastic film, such as a polyethylene terephthalate (PET) film, and reagent layer 1b, which contains a spreading layer and which is overlaid on the light transmitting substrate 1a. When necessary, a wear-resistant protective layer (not shown), which may be constituted of a fibrous material, such as a cloth, may be overlaid on the reagent layer 1b. Alternatively, the spreading layer may also serve as the protective layer.

When the dry-type frameless chemical analysis film piece 1 is in the dry state before being used for an analysis, the dry-type frameless chemical analysis film piece 1 is apt to have a bent shape with the reagent layer 1b facing the inside of the bent shape. The degree of the bending varies in accordance with the kind of the reagent layer 1b and the degree of drying of the reagent layer 1b. The reagent layer 1b of the dry-type frameless chemical analysis film piece 1 contains a reagent (containing a biochemical analytical reagent or an immunoassay reagent). When the reagent layer 1b is mixed with a specific constituent of a liquid sample spotted thereto from a sample spotting tip 88 of the sample spotting means 15 and is thereafter kept at a predetermined temperature (i.e. incubated) for a predetermined time, the reagent contained in the reagent layer 1b will undergo a color reaction. A plurality of kinds of the dry-type frameless chemical analysis film pieces 1, 1, . . . having different reagent layers 1b, 1b, are prepared depending on what the specific chemical constituent or the specific physical constituent in the liquid sample to be analyzed is.

Figure 4:
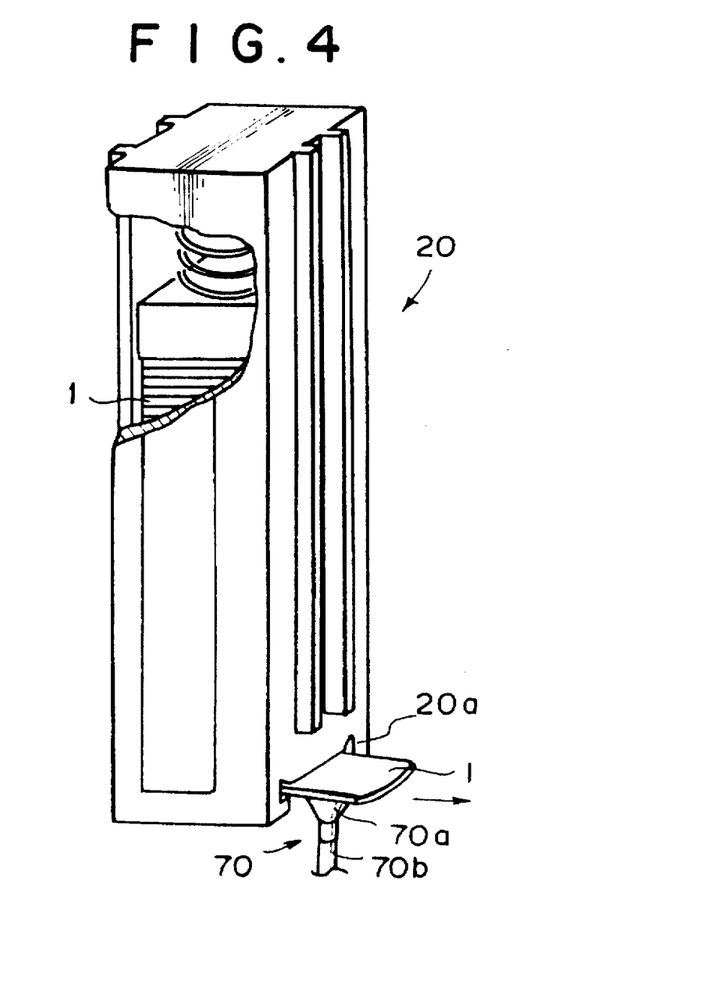
FIG. 4 is a perspective view showing how a dry-type frameless chemical analysis film piece is taken out of a cartridge.

A group of the dry-type frameless chemical analysis film pieces 1, 1, . . . to be used for the analysis of the same chemical or physical constituent are accommodated in a cartridge 20 shown in FIG. 4. The cartridge 20 accommodates a plurality of the dry-type frameless chemical analysis film pieces 1, 1, . . . stacked one upon another with the light transmitting substrate 1a facing down. As illustrated in FIG. 2, a plurality of the cartridges 20, 20, . . . are loaded in parallel relationship with one another in cartridge accommodating sections 22a, 22a, . . . which are located on the inner circumferential side or the outer circumferential side in a disk-like frame 22 of the film accommodating means 11. The frame 22 is supported on a base 24 such that it can be rotated. The frame 22 is rotated by a supplier motor (not shown), which is located at the base 24. The frame 22 is controlled such that a predetermined cartridge accommodating section 22a may be stopped at the take-out position, which corresponds to the film conveyance means 13.

The frame 22 is enclosed by a cover 25. The cartridges 20, 20, . . . are fed into and taken out of the cartridge accommodating sections 22a, 22a, . . . through feed-in openings 25a, 25a, which are formed in the upper surface of the cover 25 and are provided with lids. A dehumidifying agent accommodating section 27 is located at the center region of the frame 22. A dehumidifying agent is loaded into the dehumidifying agent accommodating section 27 through a feed-in opening 25b, which is formed at the center region in the upper surface of the cover 25 and are provided with a lid. The dehumidifying agent keeps the region inside of the film accommodating means 11 in a dry state. A shutter (not shown), which is opened when a predetermined dry-type frameless chemical analysis film piece 1 is taken out of each cartridge 20, is located at the take-out position in the lower surface of the cover 25. A take-out suction cup 70 of the film conveyance means 13 is inserted through the opened shutter and takes the lowest dry-type frameless chemical analysis film piece 1 out of the cartridge 20.

The incubator 12 is provided with a disk-like main body 40, which is rotatable and is supported by a rotation drive mechanism 41 located under the center of the main body 40. A plurality of cells 42, 42, . . . for accommodating the dry-type frameless chemical analysis film pieces 1, 1, . . . therein are located at predetermined intervals along the circumference of the main body 40. The dry-type frameless chemical analysis film pieces 1, 1, . . . are incubated in the cells 42, 42, . . .

The film conveyance means 13 conveys the dry-type frameless chemical analysis film piece 1 from the film accommodating means 11 to the incubator 12. The film conveyance means 13 is provided with the take-out suction cup 70, which takes the dry-type frameless chemical analysis film piece 1 out of the cartridge 20. The film conveyance means 13 is also provided with a U-shaped transfer member 73 serving as a transfer means. The transfer member 73 supports and receives the dry-type frameless chemical analysis film piece 1, which is being supported on the take-out suction cup 70, from below with the reagent layer 1b facing up. Thereafter, the transfer member 73 inserts the dry-type frameless chemical analysis film piece 1 into one of the cells 42, 42, . . . of the incubator 12 through its side opening. The film conveyance means 13 is further provided with a feed-in suction cup 76, which serves as a holding means. The feed-in suction cup 76 moves from below the cell 42 of the incubator 12 and holds the dry-type frameless chemical analysis film piece 1, which is being supported in the cell 42 by the transfer member 73.

As illustrated in FIG. 4, the take-out suction cup 70 is provided with a suction cup 70a, which faces up and holds the lower surface of the light transmitting substrate 1a of the dry-type frameless chemical analysis film piece 1. The suction cup 70a is supported by a conveyance base 70b and is connected through a reduced pressure pipe to a suction pump (not shown). The conveyance base 70b can be moved horizontally and vertically by a movement mechanism (not shown).

The take-out suction cup 70 is moved up and inserted through the opening, which is formed in the bottom surface of the cartridge 20. The take-out suction cup 70 thus holds the light transmitting substrate 1a of the lowest dry-type frameless chemical analysis film piece 1 accommodated in the cartridge 20. Thereafter, the take-out suction cup 70 is slightly moved down and is then moved horizontally while carrying the dry-type frameless chemical analysis film piece 1 in a bent state. The take-out suction cup 70 thus takes out the dry-type frameless chemical analysis film piece 1 horizontally through an opening 20a, which is formed in the side surface of the cartridge 20. Thereafter, the take-out suction cup 70 moves down, passes through the shutter opening of the cover 25 of the film accommodating means 11, and then moves towards the position for sample application.

Figure 5:
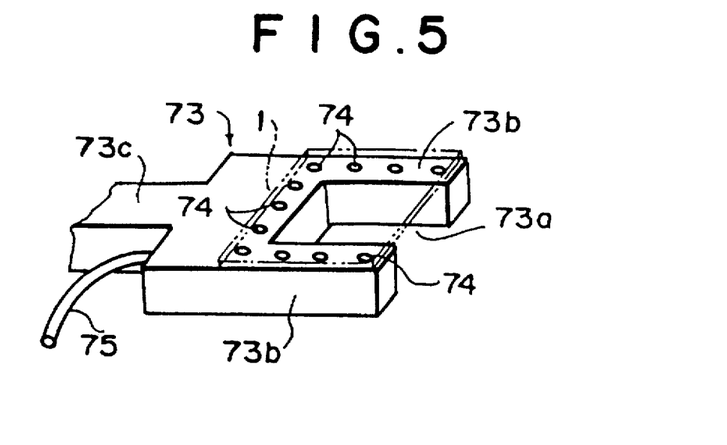
FIG. 5 is a perspective view showing the major part of a transfer member.

As illustrated in FIG. 5, the transfer member 73 is constituted of an approximately U-shaped flat plate capable of holding the dry-type frameless chemical analysis film piece 1 on the upper surface by suction. A cutaway portion 73a is formed at the center region and is defined by fork portions 73b, 73b extending forwardly on both sides of the cutaway portion 73a. Suction holes 74, 74, . . . are formed at the fork portions 73b, 73b and the back side of the cutaway portion 73a. The suction holes 74, 74, . . . are connected through a reduced pressure pipe 75 to a suction pump. A base 73c of the transfer member 73 is associated with a drive mechanism (not shown) such that the transfer member 73 can move from the position for sample application into the cell 42 of the incubator 12 through the side opening.

Figure 6A:
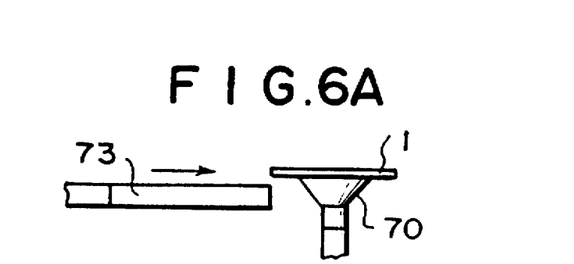
FIGS. 6A, 6B, and 6C are schematic views showing how a dry-type frameless chemical analysis film piece is transferred from a take-out suction cup to the transfer member.
Figure 6B:
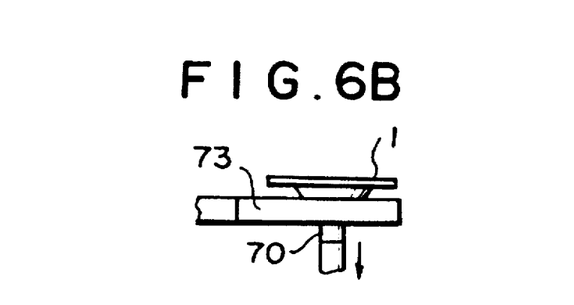
Figure 6C:
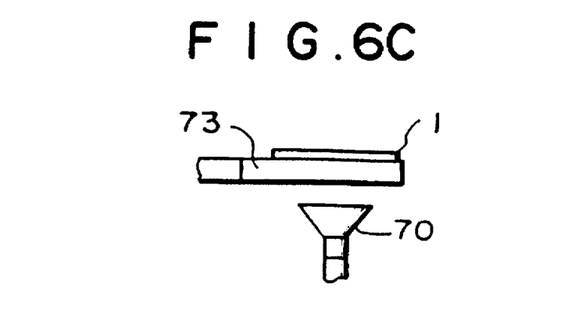

As illustrated in FIG. 6A, when the transfer member 73 is to receive the dry-type frameless chemical analysis film piece 1 from the take-out suction cup 70, the transfer member 73 is moved towards the take-out suction cup 70, which holds the dry-type frameless chemical analysis film piece 1. Thereafter, as illustrated in FIG. 6B, the transfer member 73 is stopped when the take-out suction cup 70 is located in the region inside of the cutaway portion 73a and the dry-type frameless chemical analysis film piece 1 is located above the transfer member 73. The take-out suction cup 70 is then moved down. In this manner, as illustrated in FIG. 6C, the dry-type frameless chemical analysis film piece 1, which was held by the take-out suction cup 70, is held through suction by the fork portions 73b, 73b and the periphery of the cutaway portion 73a of the transfer member 73. The dry-type frameless chemical analysis film piece 1 is accurately held at the predetermined position on the take-out suction cup 70. Therefore, the dry-type frameless chemical analysis film piece 1 is accurately held at the predetermined position on the transfer member 73. A predetermined amount of the liquid sample is spotted by the sample spotting means 15 onto the center region of the reagent layer 1b of the dry-type frameless chemical analysis film piece 1, which is being held by the transfer member 73.

As illustrated in FIG. 2, the liquid sample accommodating means 14 is provided with a rotatable table 85, which is rotated by a rotation drive mechanism 86. A plurality of sample tubes 87, 87, . . ., which accommodate liquid samples, are supported at the outer circumferential region of the rotatable table 85 and successively moved to the position for supply of the liquid sample. A plurality of sample spotting tips 88, 88, . . . , each of which is to be fitted to the bottom end of a sample spotting nozzle 91, are accommodated in the inner circumferential region of the rotatable table 85.

The sample spotting means 15 spots the liquid sample from each of the sample tubes 87 onto the dry-type frameless chemical analysis film piece 1 before being conveyed to the incubator 12. The sample spotting means 15 is provided with the sample spotting nozzle 91, which sucks and discharges the liquid sample. The pipette-like sample spotting tip 88 is releasably fitted to the bottom end of the sample spotting nozzle 91. The sample spotting tip 88 can be moved vertically and can be swung by a drive mechanism 92. The sample spotting tip 88 sucks up the liquid sample from the liquid sample accommodating means 14, moves and spots the liquid sample onto dry-type frameless chemical analysis film piece 1, which is held on the transfer member 73. When a different liquid sample is to be spotted, the sample spotting tip 88 fitted to the bottom end of the sample spotting nozzle 91 of the sample spotting means 15 is exchanged with a new one.

Figure 1:
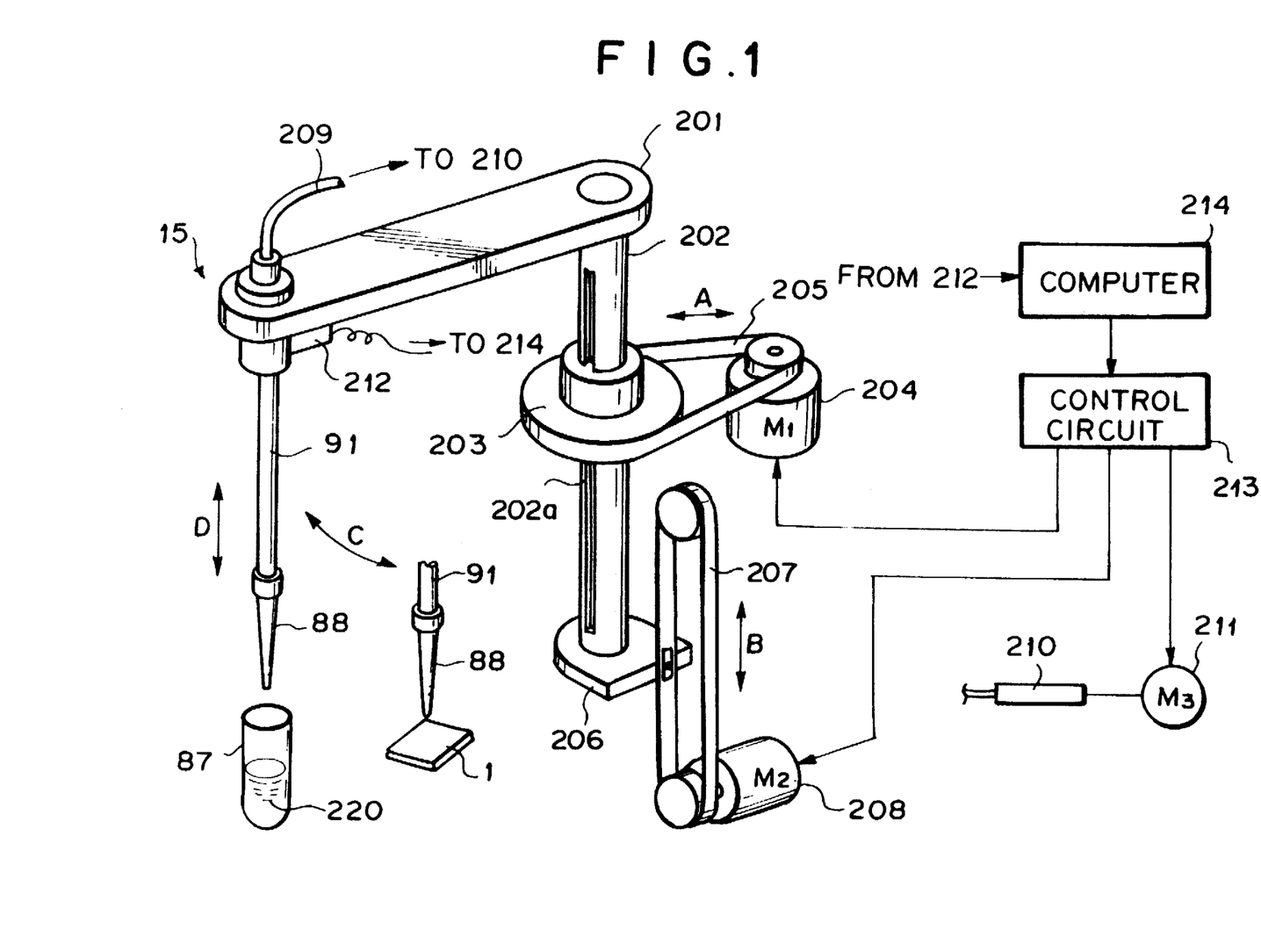
FIG. 1 is a schematic view showing an embodiment of the apparatus for spotting liquid samples onto dry-type frameless chemical analysis film pieces in accordance with the present invention.

The sample spotting means 15 is constituted as shown in FIG. 1. Specifically, the sample spotting means 15 is provided with a sampling arm 201, which supports the sample spotting nozzle 91 at one end thereof such that the sample spotting nozzle 91 can be moved vertically. The sample spotting means 15 is also provided with a spline shaft 202, which extends vertically and which supports the sampling arm 201 in the horizontal orientation at the other end of the sampling arm 201. The sample spotting means 15 is further provided with a belt pulley 203 having a small-diameter portion and a large-diameter portion. The belt pulley 203 is provided with a claw, which is engaged with a groove 202a formed in the side wall of the spline shaft 202 along its axial direction. Also, the belt pulley 203 is secured to the spline shaft 202 with respect to the rotating direction and can be moved along the axial direction of the spline shaft 202. The sample spotting means 15 is still further provided with a belt 205, and a first motor 204, which moves the belt 205 along predetermined directions indicated by the double headed arrow A and thereby rotates the belt pulley 203 by a predetermined amount in the predetermined directions. The sample spotting means 15 is also provided with a collar 206, which is secured to the bottom of the spline shaft 202, and a belt 207, which is secured by a screw to the side wall of the collar 206. The sample spotting means 15 is further provided with a second motor 208, which moves the belt 207 along predetermined directions indicated by the double headed arrow B and thereby moves the spline shaft 202 vertically by a predetermined length.

The sample spotting means 15 is still further provided with a hose 209, a syringe 210, and a third motor 211, which adjust the pressure in the air path in the region inside of the sample spotting nozzle 91 and the pressure inside the sample spotting tip 88. The sample spotting means 15 is also provided with a nozzle vertical movement sensor 212, which detects the vertical movement of the sample spotting nozzle 91.

The sample spotting means 15 is further provided with a control circuit 213, which controls the motors 204, 208, and 211. The sample spotting means 15 is still further provided with a computer 214, which receives a detection signal from the nozzle vertical movement sensor 212 and feeds a predetermined motor control signal to the control circuit 213 in accordance with a predetermined sequence program.

Figure 7A:
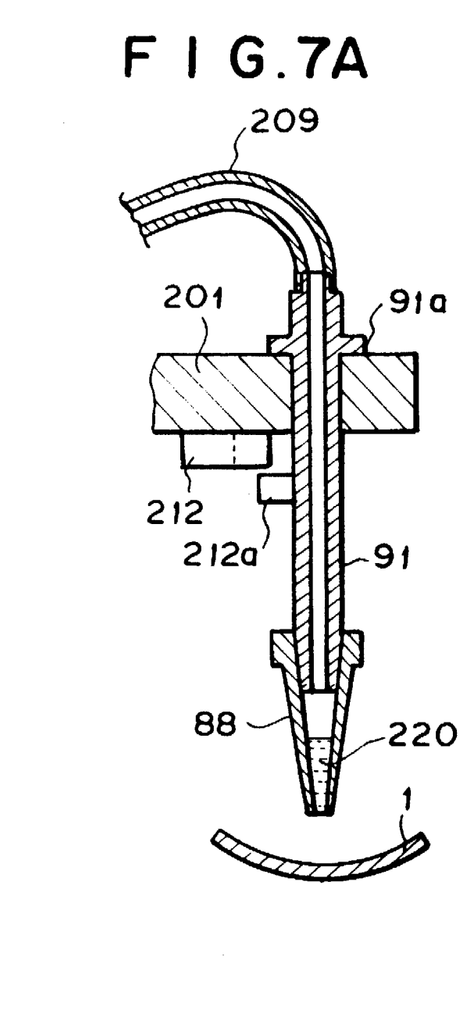
FIGS. 7A, 7B, and 7C are schematic views showing an embodiment of the method for spotting liquid samples onto dry-type frameless chemical analysis film pieces in accordance with the present invention.
Figure 7B:
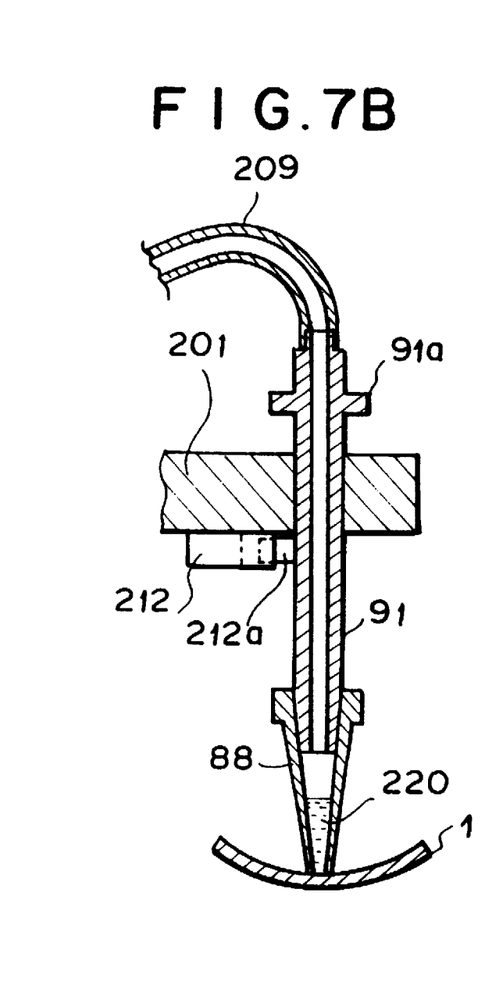
Figure 7C:
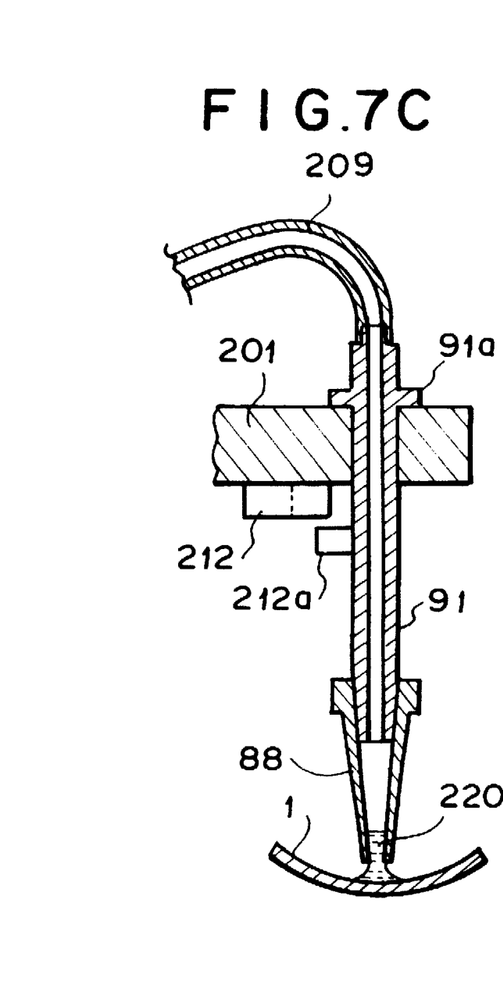

How the liquid sample is spotted onto the dry-type frameless chemical analysis film piece 1 in the embodiment described above will be described hereinbelow with reference to FIGS. 7A, 7B, and 7C. Specifically, as illustrated in FIG. 7A, the sample spotting tip 88, in which a liquid sample 220 has been accommodated, is moved from its original position and is set at the position above the dry-type frameless chemical analysis film piece 1. Thereafter, the sampling arm 201 is moved down. As illustrated in FIG. 7B, when the bottom end of the sample spotting tip 88 comes into contact with the dry-type frameless chemical analysis film piece 1, the sample spotting tip 88 is supported by the dry-type frameless chemical analysis film piece 1, and the downward movement of the sample spotting tip 88 is ceased. At this time, the sampling arm 201 continues to move down for a certain length of time. In this manner, a flag 212a is inserted into a slit of the nozzle vertical movement sensor 212, and light is thereby blocked from impinging upon a light receiving section of the nozzle vertical movement sensor 212. Therefore, it is detected that the bottom end of the sample spotting tip 88 has been brought into contact with the dry-type frameless chemical analysis film piece 1. Thereafter, the sampling arm 201 is moved up. At this time, since a collar 91a of the sample spotting nozzle 91 is not in contact with the upper surface of the sampling arm 201, the bottom end of the sample spotting tip 88 is kept in the state supported on the dry-type frameless chemical analysis film piece 1. The flag 212a is then moved away from the slit of the nozzle vertical movement sensor 212, and light is thereby caused to impinge upon the light receiving section of the nozzle vertical movement sensor 212. As a result, it is detected that the bottom end of the sample spotting tip 88 has been separated from the dry-type frameless chemical analysis film piece 1. The timing, with which the flag 212a is completely separated from the slit of the nozzle vertical movement sensor 212, is adjusted such that it may approximately coincide with the timing, with which the collar 91a of the sample spotting nozzle 91 comes into contact with the upper surface of the sampling arm 201. Thereafter, as illustrated in FIG. 7C, the sample spotting tip 88 is moved up together with the sample spotting nozzle 91, and the liquid sample 220 is discharged from the sample spotting tip 88 at a predetermined rate onto the dry-type frameless chemical analysis film piece 1. At this time, the speed, with which the sample spotting tip 88 is moved up, and the rate, with which the liquid sample 220 is discharged from the sample spotting tip 88 onto the dry-type frameless chemical analysis film piece 1, are controlled in accordance with the spreading speed of the liquid sample 220 on the dry-type frameless chemical analysis film piece 1, the viscosity of the liquid sample 220, and the like, such that the liquid sample 220 may not break when being discharged and such that the liquid sample 220 having been discharged may not cling to the outer side wall of the bottom end of the sample spotting tip 88 due to a rise in the level of the discharged liquid sample 220 on the dry-type frameless chemical analysis film piece 1.

Figure 8:
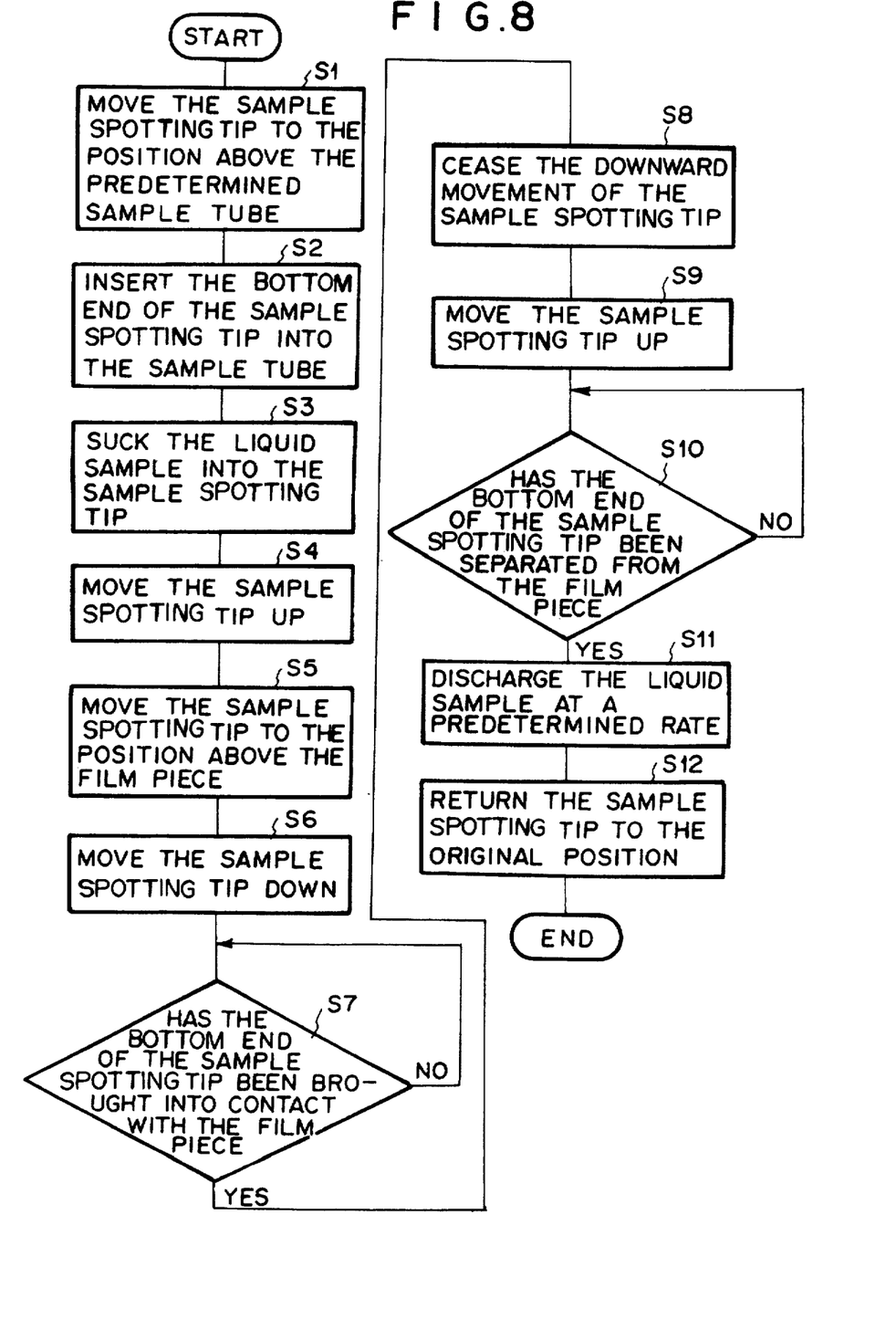

How the computer 214 works will be described hereinbelow with reference to FIG. 8. Specifically, in a step S1, a predetermined motor drive signal is fed from the control circuit 213 to the first motor 204, and the first motor 204 is thereby rotated. The sampling arm 201 is thus swung in one of the directions indicated by the double headed arrow C, and the sample spotting tip 88 is thereby located above the sample tube 87.

Thereafter, in a step S2, a predetermined motor drive signal is fed from the control circuit 213 to the second motor 208, and the second motor 208 is thereby rotated. The sampling arm 201 is thus moved down as indicated by the double headed arrow D, and the bottom end of the sample spotting tip 88 is thereby immersed into the liquid sample 220 contained in the sample tube 87.

Thereafter, in a step S3, a predetermined motor drive signal is fed from the control circuit 213 to the third motor 211, and the third motor 211 is thereby rotated. The syringe 210 is thus activated by the rotation of the third motor 211. By the operation of the syringe 210, the pressure inside the hose 209, in the air path of the sample spotting nozzle 91, and in the region inside of the sample spotting tip 88 becomes a negative pressure. As a result, the liquid sample 220 is sucked from the bottom end of the sample spotting tip 88 into the region inside of the sample spotting tip 88.

Thereafter, in a step S4, a predetermined motor drive signal is fed from the control circuit 213 to the second motor 208, and the second motor 208 is thereby rotated. The sampling arm 201 and the sample spotting tip 88 are thereby moved up. Thereafter, in a step S5, a predetermined motor drive signal is fed from the control circuit 213 to the first motor 204, and the first motor 204 is thereby rotated. The sampling arm 201 is thus swung, and the sample spotting tip 88 is thereby moved to the position above the dry-type frameless chemical analysis film piece 1.

Thereafter, in a step S6, a predetermined motor drive signal is fed from the control circuit 213 to the second motor 208, and the second motor 208 is thereby rotated. The sampling arm 201 and the sample spotting tip 88 are thus moved down.

Thereafter, in a step S7, the computer 214 waits for an entry of a signal, which indicates that the bottom end of the sample spotting tip 88 has been brought into contact with the dry-type frameless chemical analysis film piece 1, from the nozzle vertical movement sensor 212. In a step S8, when the computer 214 receives the signal, a predetermined motor drive signal is fed from the control circuit 213 to the second motor 208, and the rotation of the second motor 208 is thereby ceased temporarily. In this manner, the downward movement of the sampling arm 201 is ceased. Thereafter, in a step S9, the second motor 208 is rotated reversely, and the sampling arm 201 is moved up.

In a step S10, the computer 214 waits for an entry of a signal, which indicates that the bottom end of the sample spotting tip 88 has been separated from the dry-type frameless chemical analysis film piece 1, from the nozzle vertical movement sensor 212. In a step S11, when the computer 214 receives the signal, a predetermined motor drive signal is fed from the control circuit 213 to the third motor 211, and the third motor 211 is thereby rotated. The syringe 210 is thus activated by the rotation of the third motor 211. By the operation of the syringe 210, the pressure inside the hose 209, in the air path of the sample spotting nozzle 91, and in the region inside of the sample spotting tip 88 becomes a positive pressure. As a result, the liquid sample 220 is discharged from the sample spotting tip 88 at a predetermined rate onto the dry-type frameless chemical analysis film piece 1.

Thereafter, in a step S12, predetermined motor drive signals are fed from the control circuit 213 to the first motor 204 and the second motor 208 such that the sample spotting tip 88 may be returned to the original position and can then be used for the next sample spotting process.

The speed, with which the sampling arm 201 is moved up in the step S9, and the rate, with which the liquid sample 220 is discharged from the sample spotting tip 88 onto the dry-type frameless chemical analysis film piece 1 in the step S11, are controlled by appropriately setting the rotation speeds of the second motor 208 and the third motor 211 in accordance with the spreading speed of the liquid sample 220 on the dry-type frameless chemical analysis film piece 1, the viscosity of the liquid sample 220, and the like, such that the liquid sample 220 may not break when being discharged and such that the liquid sample 220 having been discharged may not cling to the outer side wall of the bottom end of the sample spotting tip 88 due to a rise in the level of the discharged liquid sample 220 on the dry-type frameless chemical analysis film piece 1.

For example, in cases where the liquid sample 220 is the plasma constituent and the dry-type frameless chemical analysis film piece 1 is of the type used for the lactic acid dehydrase (LDH-P), the rotation speeds of the second motor 208 and the third motor 211 are controlled such that the speed, with which the sampling arm 201 is moved up in the step S9, may be 2 mm/s, and the rate, with which the liquid sample 220 is discharged from the sample spotting tip 88 onto the dry-type frameless chemical analysis film piece 1 in the step S11, may be 200 mm/s.

Also, in this embodiment, the nozzle vertical movement sensor 212 detects that the sample spotting tip 88 has been brought into contact with the dry-type frameless chemical analysis film piece 1. In accordance with the detection signal, the speed, with which the sampling arm 201 is moved up, and the rate (the timing), with which the liquid sample 220 is discharged from the sample spotting tip 88 onto the dry-type frameless chemical analysis film piece 1, are controlled. However, the nozzle vertical movement sensor 212 need not necessarily be used. Specifically, the position, at which the sampling arm 201 is stopped, may be set at the position illustrated in FIG. 7B. Thereafter, the sampling arm 201 may be moved up, and a discharging pressure may be applied to the region inside of the sample spotting tip 88 while the sampling arm 201 is being moved up. In this manner, the liquid sample 220 may be discharged from the bottom end of the sample spotting tip 88 at the time at which the bottom end of the sample spotting tip 88 begins separating from the dry-type frameless chemical analysis film piece 1.

Further, as in the embodiment shown in FIGS. 9A through 9E, after the liquid sample 220 has been sucked into the sample spotting tip 88, a small amount of air may be sucked, and an air layer may thereby be formed in the bottom end of the sample spotting tip 88.

Figure 9A:
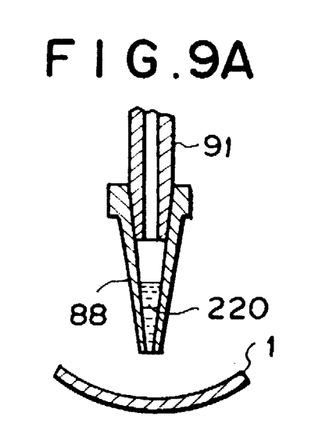
Figure 9B:
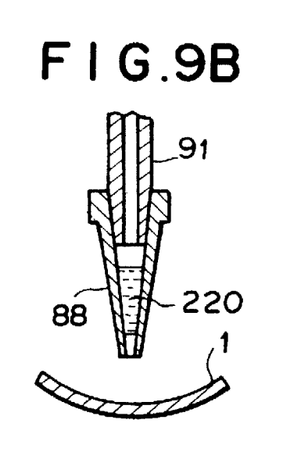

Specifically, in this embodiment, as illustrated in FIG. 9A, the sample spotting tip 88, in which the liquid sample 220 has been accommodated, is moved to the position exactly above the dry-type frameless chemical analysis film piece 1. Thereafter, the third motor 211 is rotated, and the syringe 210 is thereby activated in order to set a negative pressure in the air path in the sample spotting nozzle 91. In this manner, as illustrated in FIG. 9B, a small amount of air is sucked into the bottom end of the sample spotting tip 88.

Figure 9C:
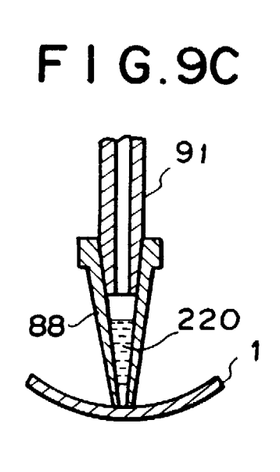
Figure 9D:
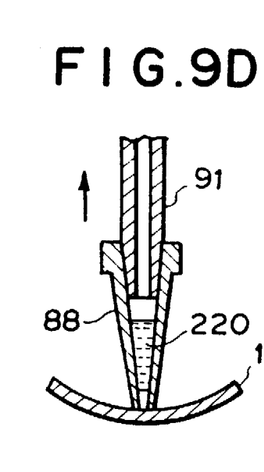

Thereafter, as illustrated in FIG. 9C, the sample spotting tip 88 is moved down, and its bottom end is brought into contact with the dry-type frameless chemical analysis film piece 1. As illustrated in FIG. 9D, the sample spotting tip 88 is then moved up in accordance with the detection of the contact state. Also, the pressure in the air path in the sample spotting nozzle 91 is set at a positive pressure, and the discharge of the liquid sample 220 is begun.

Figure 9E:
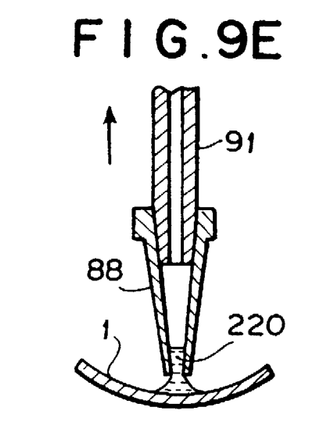

However, as described above, the air layer has been formed in the bottom end of the sample spotting tip 88. Therefore, at the time at which the bottom end of the sample spotting tip 88 begins separating from the surface of the dry-type frameless chemical analysis film piece 1, air is discharged from the bottom end of the sample spotting tip 88. As illustrated in FIG. 9E, when the bottom end of the sample spotting tip 88 has separated a predetermined distance from the surface of the dry-type frameless chemical analysis film piece 1, the liquid sample 220 is discharged from the bottom end of the sample spotting tip 88 onto the dry-type frameless chemical analysis film piece 1.

Thereafter, while the sample spotting tip 88 is being moved up, the predetermined amount of the liquid sample 220 is discharged from the sample spotting tip 88.

In this embodiment, wherein the air layer is formed in the bottom end of the sample spotting tip 88, at the time at which the surface of the dry-type frameless chemical analysis film piece 1 is wetted with the liquid sample 220, the bottom end of the sample spotting tip 88 is not in contact with the surface of the dry-type frameless chemical analysis film piece 1. Therefore, a substance in the surface of the dry-type frameless chemical analysis film piece 1 can be prevented from clinging to the bottom end of the sample spotting tip 88 and serving as an impurity during the next sample spotting process.

As illustrated in FIG. 2, the dry-type frameless chemical analysis film piece 1, to which the liquid sample 220 has been spotted, is incubated in the incubator 12, and the optical density of the dry-type frameless chemical analysis film piece 1 is measured with the measurement means 16, which is located under the incubator 12. The measurement means 16 is provided with a probe 95 for finding the optical density, which depends on how much of a reaction product was formed by the reaction between the liquid sample 220 and the reagent in the dry-type frameless chemical analysis film piece 1. The probe 95 irradiates measuring light, which contains light having predetermined wavelengths, through the light transmitting substrate 1a to the reagent layer 1b of the dry-type frameless chemical analysis film piece 1. A photodetecting element of the probe 95 measures the amount of light reflected by the reagent layer 1b. Light is produced by a light source (lamp) 96 and irradiated through one of a plurality of filters 97, 97, . . . to the probe 95. The light is irradiated through the probe 95 to the reagent layer 1b. Many kinds of the filters 97, 97, . . . are prepared in the disk 98 depending on what the specific chemical or physical constituent to be analyzed is. The disk 98 is rotated by a motor 99, and a filter 97 having predetermined characteristics corresponding to the specific chemical or physical constituent to be analyzed is thereby selected.

The light reflected by the reagent layer 1b carries optical information (specifically, the amount of light) corresponding to the amount of a coloring matter formed in the reagent layer 1b. The reflected light carrying the optical information impinges upon the photodetecting element of the probe 95 and is photoelectrically converted into an electric signal. The electric signal obtained in this manner is passed through an amplifier (not shown) and fed into a judgment section (not shown). The judgment section makes a judgment as to the optical density of the coloring matter, which has been formed in the reagent layer 1b, from the level of the received electric signal. The concentration of the specific biochemical substance in the liquid sample 220 is thereby determined.

The measurement with the biochemical analysis system 10 is carried out in the manner described below. First, the take-out suction cup 70 of the film conveyance means 13 takes a dry-type frameless chemical analysis film piece 1 out of a cartridge 20, which is accommodated in the film accommodating means 11 and which corresponds to the specific biochemical substance to be analyzed. The dry-type frameless chemical analysis film piece 1, which is held by the take-out suction cup 70, is transferred to the transfer member 73 with the reagent layer 1b facing up. Thereafter, the liquid sample 220 is spotted onto the reagent layer 1b of the dry-type frameless chemical analysis film piece 1.

Also, as illustrated in FIG. 2, a film discharging means 17 is located at the position for film discharge in the incubator 12. The film discharging means 17 comprises a film discharging suction cup 81, which holds and raises the dry-type frameless chemical analysis film piece 1 having been measured in the cell 42. The film discharging means 17 also comprises an approximately U-shaped transfer member 82, which receives the dry-type frameless chemical analysis film piece 1 having been raised by the film discharging suction cup 81 and conveys it to the exterior of the incubator 12. The film discharging means 17 further comprises a discarding suction cup 83, which receives the dry-type frameless chemical analysis film piece 1 having been taken out by the transfer member 82 and discards it into a waste film box 84.

The method and apparatus for spotting liquid samples onto dry-type frameless chemical analysis film pieces in accordance with the present invention are not limited to the embodiments described above and may be embodied in various other ways.

Figure 10A:
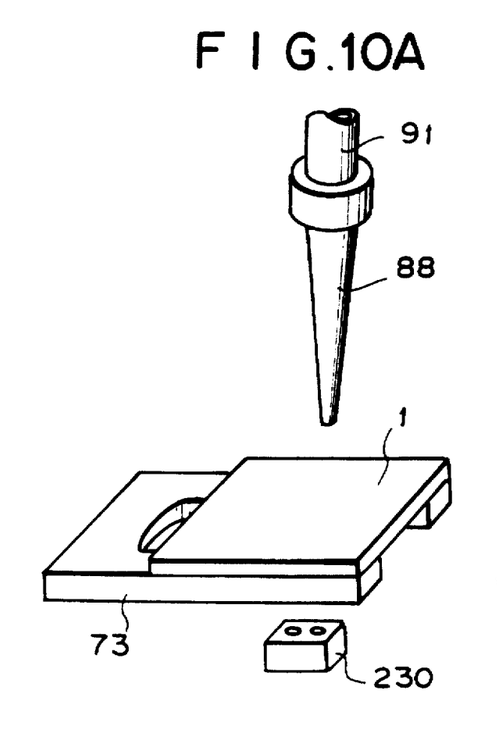
FIGS. 10A and 10B are perspective views showing a modification of a sensor shown in FIG. 1.
Figure 10B:
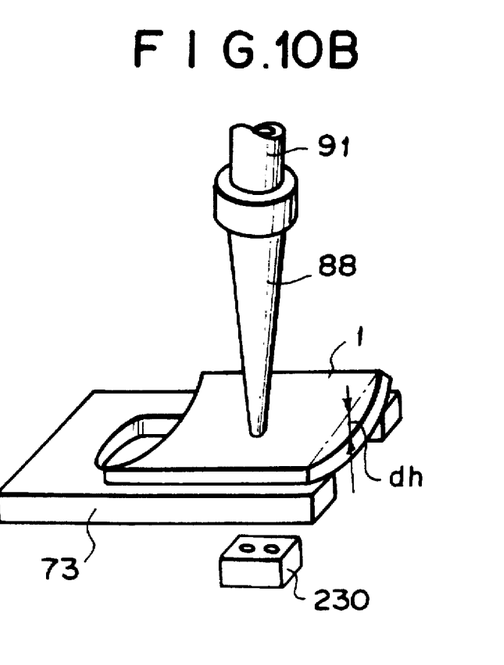

For example, as the sensor for detecting that the liquid sample suction nozzle (the sample spotting nozzle 91) has been brought into contact with the dry-type frameless chemical analysis film piece 1 and that it has separated from the dry-type frameless chemical analysis film piece 1, a reflection type of optical sensor 230 shown in FIGS. 10A and 10B may be employed in lieu of the nozzle vertical movement sensor 212.

Figure 11:
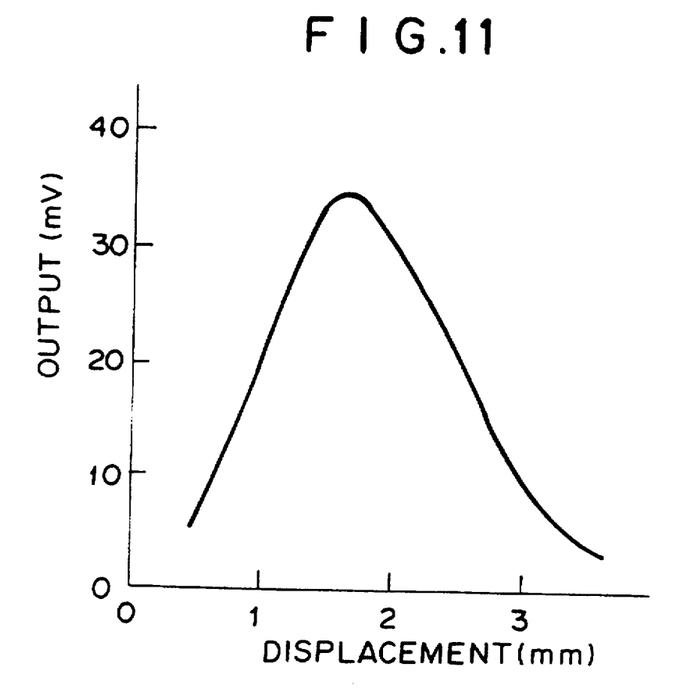
FIG. 11 is a graph showing an example of the output characteristics of the reflection type of optical sensor shown in FIG. 10.

Specifically, as described above, at the position for sample application, the dry-type frameless chemical analysis film piece 1 is placed on and held by the U-shaped transfer member 73. In this state, the portion of the dry-type frameless chemical analysis film piece 1, which is brought into contact with the bottom end of the sample spotting tip 88, corresponds to the central cutaway portion of the transfer member 73. As illustrated in FIG. 10B, when the bottom end of the sample spotting tip 88 comes into contact with the dry-type frameless chemical analysis film piece 1 and further moves down, the dry-type frameless chemical analysis film piece 1 is bent in a downwardly convex shape. As illustrated in FIG. 11, the reflection type of optical sensor 230 has the characteristics such that its output is highest when the object of measurement is located at a predetermined distance (approximately 1.7 mm). As illustrated in FIG. 10A, when the sample spotting tip 88 is not in contact with the dry-type frameless chemical analysis film piece 1, the distance between the lower surface of the dry-type frameless chemical analysis film piece 1 (actually, at this time, the dry-type frameless chemical analysis film piece 1 is in a slightly bent state) and the reflection type of optical sensor 230 is set to be equal to the predetermined distance (approximately 1.5 mm).

As illustrated in FIG. 10B, when the dry-type frameless chemical analysis film piece 1 is bent in the downwardly convex shape by the sample spotting tip 88, the distance between the reflection type of optical sensor 230 and the lower surface of the dry-type frameless chemical analysis film piece 1 becomes smaller by a length dh than the predetermined distance described above. Therefore, the output generated by the reflection type of optical sensor 230 becomes low. From the change in the output of the reflection type of optical sensor 230, it can be detected that the sample spotting tip 88 has been brought into contact with the dry-type frameless chemical analysis film piece 1.

Figure 12:
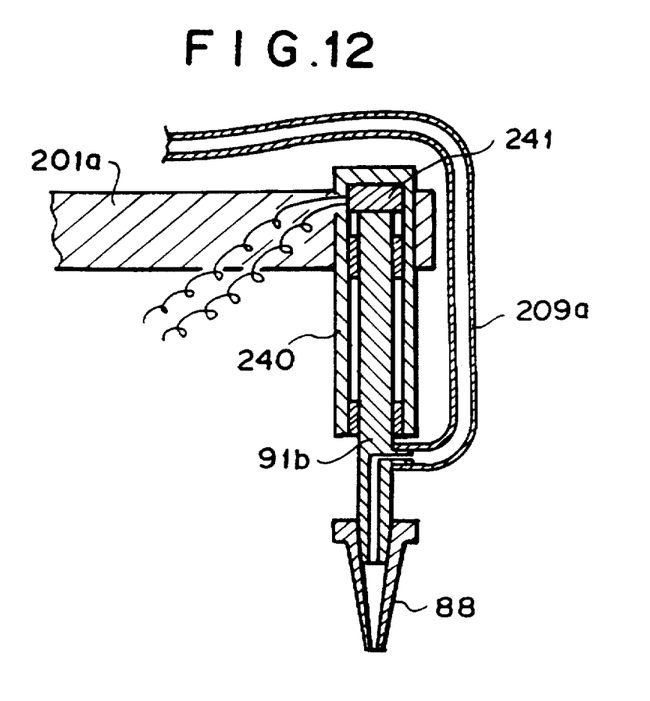
FIG. 12 is a schematic view showing a different modification of the sensor shown in FIG. 1.

Also, as the sensor, as illustrated in FIG. 12, a pressure sensor 241 may be employed. The pressure sensor 241 is located on a sample spotting nozzle 91b, which slides with respect to a sampling arm 201a.

Specifically, the pressure sensor 241 and the upper part of the sample spotting nozzle 91b are accommodated in a cover 240. When the sample spotting tip 88 is brought into contact with the dry-type frameless chemical analysis film piece 1, the pressure sensor 241 is sandwiched between the sample spotting nozzle 91b and the inner surface of the upper wall of the cover 240. From the output of the pressure sensor 241, it can be detected that the sample spotting tip 88 has been brought into contact with the dry-type frameless chemical analysis film piece 1.

In such cases, a hose 209a should preferably be connected to the air path at the side wall part of the sample spotting nozzle 91b.

Two independent sensors may be utilized in order to detect that the liquid sample suction nozzle (the sample spotting nozzle 91) has been brought into contact with the dry-type frameless chemical analysis film piece 1 and that it has separated from the dry-type frameless chemical analysis film piece 1.

The speed, at which the sample spotting tip 88 is moved up after being brought into contact with the dry-type frameless chemical analysis film piece 1, and the rate, with which the liquid sample 220 is discharged onto the dry-type frameless chemical analysis film piece 1, may not necessarily be constant and may be varied in accordance with predetermined patterns.

Furthermore, two independent means may be utilized in order to move the sample spotting tip 88 down and to move it up. Alternatively, for example, the sample spotting tip 88 may be moved down by gravity by releasing the holding of the sample spotting tip 88.

What is claimed is:

1. A method for spotting liquid samples onto dry frameless chemical analysis film pieces, the dry frameless chemical analysis film pieces tending to bend varying amounts from film piece to film piece such that a position of a film surface of each film piece in turn tends to vary for different film pieces, comprising the steps of:

i) sucking a predetermined amount of a liquid sample into a sample spotting tip which includes a bottom end and which is fitted to a bottom end of a suction nozzle for sucking the liquid sample, ii) moving the sample spotting tip down, the bottom end of the sample spotting tip being thereby brought into contact with a dry frameless chemical analysis film piece, said contact of the bottom end of the sample spotting tip with the dry frameless chemical analysis film piece being detected by detecting an amount of the bend of the dry frameless chemical analysis film piece, iii) moving the sample spotting tip up, and iv) increasing a pressure inside the sample spotting tip, while the sample spotting tip is thus being moved up, whereby the liquid sample is discharged from the sample spotting tip onto the dry frameless chemical analysis film piece, wherein after the predetermined amount of the liquid sample has been sucked into the sample spotting tip, but before the bottom end of the sample spotting tip is brought into contact with the dry frameless chemical analysis film piece, the pressure inside the sample spotting tip is further reduced to a negative pressure, and air is thereby sucked into the bottom end portion in the sample spotting tip.

2. A method as defined in claim 1 wherein, when the liquid sample is discharged from the sample spotting tip onto the dry frameless chemical analysis film piece, further comprising increasing or decreasing a speed, with which the sample spotting tip is moved up, and increasing or decreasing the pressure inside the sample spotting tip based on parameters including a spreading speed of the liquid sample on the dry frameless chemical film piece, and a viscosity of the liquid sample.

* * * * *